United States Patent [19]

Goetz

[11] 4,200,765

[45] Apr. 29, 1980

[54] GLYCOL ALDEHYDE AND ETHYLENE GLYCOL PROCESSES

[75] Inventor: Richard W. Goetz, Cincinnati, Ohio

[73] Assignee: National Distillers and Chemical Corporation, New York, N.Y.

[21] Appl. No.: 884,877

[22] Filed: Mar. 9, 1978

Related U.S. Application Data

[63] Continuation-in-part of Ser. No. 724,126, Sep. 17, 1976, abandoned.

[30] Foreign Application Priority Data

Sep. 12, 1977 [IE] Ireland .................................. 1874/77

[51] Int. Cl.² .................... C07C 29/14; C07C 31/20; C07C 47/19
[52] U.S. Cl. ..................................... 568/862; 260/602; 568/840; 568/852; 260/340.6; 260/340.9 R
[58] Field of Search ................ 260/602; 568/852, 861, 568/862, 840

[56] References Cited

U.S. PATENT DOCUMENTS

| | | | |
|---|---|---|---|
| 2,451,333 | 10/1948 | Gresham et al. | 568/862 |
| 2,639,297 | 3/1953 | Whetstone et al. | 568/866 |
| 2,888,492 | 5/1955 | Fischer et al. | 568/865 |
| 3,560,539 | 2/1971 | Booth | 252/431 P |
| 3,769,331 | 10/1973 | Kuckertz et al. | 568/862 |
| 3,833,634 | 9/1974 | Pruett et al. | 260/449.5 |
| 3,917,661 | 11/1975 | Pruett et al. | 260/598 |
| 3,920,753 | 11/1975 | Yukawa et al. | 260/602 |
| 3,948,965 | 4/1976 | Cawse | 260/449.5 |
| 4,079,085 | 3/1978 | Wall | 260/615 R |

OTHER PUBLICATIONS

Vysotskii et al., Chem. Abs. 77 (1972) 163948u.

*Primary Examiner*—Howard T. Mars
*Attorney, Agent, or Firm*—Kenneth D. Tremain

[57] ABSTRACT

A process for preparing glycol aldehyde by reacting formaldehyde, hydrogen and carbon monoxide at elevated temperature and superatmospheric pressure in the presence of rhodium catalyst and conversion thereof to ethylene glycol as the substantially exclusive polyol product.

24 Claims, No Drawings

GLYCOL ALDEHYDE AND ETHYLENE GLYCOL PROCESSES

This application is a continuation-in-part of U.S. application Ser. No. 724,126, filed Sept. 17, 1976 and now abandoned.

This invention is concerned with processes for the preparation of glycol aldehyde, and conversion thereof to ethylene glycol, by reaction of formaldehyde, carbon monoxide and hydrogen in the presence of a rhodium catalyst.

Ethylene glycol is a very valuable commercial chemical with a wide variety of uses including use as a coolant and anti-freeze, monomer for polyester production, solvent, and an intermediate for production of commercial chemicals.

Glycol aldehyde is a valuable intermediate in organic synthesis, including the preparation of serine, and is particularly useful as an intermediate in the production of ethylene glycol by catalytic hydrogenation.

The reaction of formaldehyde with carbon monoxide and hydrogen is a known reaction and yields, inter alia, ethylene glycol, methanol, and higher polyhydroxy compounds. For example, U.S. Pat. No. 2,451,333 describes the reaction of formaldehyde, carbon monoxide and hydrogen over a cobalt catalyst to produce mixtures of polyhydroxy compounds which include ethylene glycol, glycerol, and higher polyols. Various metal catalysts are also disclosed including nickel, manganese, iron, chromium, copper, platinum, molybdenum, palladium, zinc, cadmium, ruthenium and compounds thereof.

U.S. Pat. No. 3,920,753 describes the production of glycol aldehyde by reaction of formaldehyde with carbon monoxide and hydrogen in the presence of a cobalt catalyst under controlled reaction conditions, but with comparatively low yields.

Polyols are also produced by reaction of carbon monoxide and hydrogen over various metal catalysts. U.S. Pat. No. 3,833,634 describes this reaction catalyzed by rhodium to produce ethylene glycol, propylene glycol, glycerol, methanol, ethanol, methyl acetate, etc. Rhodium catalysts are also employed in the production of oxygenated derivatives of alkenes, alkadienes and alkenoic acid ester by reaction with carbon monoxide and hydrogen, as described, for example, in U.S. Pat. Nos. 3,081,357; 3,527,809; 3,544,635; 3,557,219; and 3,917,661.

The prior art processes for production of ethylene glycol have characteristically provided mixtures of products, the principal co-products being propylene glycol and glycerine, along with the lower alcohols, methyl and ethyl alcohol. Thus, these processes are encumbered by the need for expensive and time-consuming separation techniques where ethylene glycol is the desired product. In addition, the efficiency of the reaction in terms of yield of ethylene glycol is not high due to the concomitant formation of the co-products, which are usually present in significant amounts.

It has now been found that the reaction of formaldehyde, carbon monoxide and hydrogen over rhodium catalyst appears to involve a two-stage reaction, with the first stage yielding glycol aldehyde and methanol, and the second stage yielding ethylene glycol. Thus, this reaction is analogous to that realized with cobalt catalysts as collectively disclosed in the aforementioned U.S. Pat. Nos. 2,451,333 and 3,920,753, the surprising difference residing in the high selectivity of the present inventive process which exclusively leads to ethylene glycol as the sole detectable polyol obtained in the second stage of the reaction. Further, the conversion to glycol aldehyde realized in the first stage of the present process is substantially greater than that obtained in the process described in U.S. Pat. No. 3,920,753.

Thus, in the preferred forms of the invention, the present process provides glycol aldehyde in substantially higher yield than heretofore attainable from formaldehyde, carbon monoxide and hydrogen, provides ethylene glycol as the exclusive, detectable polyol product, in improved yields when compared to similar processes.

The very desirable results obtained in accordance with the present process renders the process particularly amenable to commercial production of ethylene glycol, not only from the viewpoint of attainable high yields of ethylene glycol, but also the ease of recovery of ethylene glycol from the co-produced methanol, e.g., by simple fractional distillation. The ease of recovery is extremely important since it permits separation of the ethylene glycol from the product mixture even in those process runs where methanol may be produced as the major product, the glycol being the minor product. Thus, even where the glycol is present in amounts corresponding to about 10 mole-percent, and even less, of the reaction product mixture, the ease of separation will permit recovery of the glycol.

Glycol aldehyde is also produced in a high order of purity. Usually, the first stage reaction mixture can be used as such in the second stage reaction mixture can be used as such in the second stage to produce ethylene glycol by reduction of glycol aldehyde to obtain the glycol as the sole polyol product.

It is, of course, axiomatic that prior art procedures are seriously encumbered by the fact that the reaction product is a mixture of polyols (including ethylene glycol) which are extremely difficult to separate even when employing multiple fractional distillations.

The process of the present invention is accomplished by contacting formaldehyde, carbon monoxide and hydrogen, preferably in a suitable solvent, in the presence of a rhodium-containing catalyst at elevated temperature and superatmospheric pressure. The major product of the two stage reaction is ethylene glycol, with the major by-product being methanol. The manner of contact is not critical since any of the various procedures normally employed in this type of reaction can be used as long as efficient gas-liquid contact is provided. Thus, the process may be carried out by contacting a solution of formaldehyde together with the rhodium catalyst with a mixture of carbon monoxide and hydrogen at the selected conditions. Alternatively, the solution of formaldehyde may be passed over the catalyst in a trickle phase under a mixture of carbon monoxide and hydrogen at the selected conditions of temperature and pressure.

In view of the two-stage nature of the present process to produce ethylene glycol, the implementation can take several forms. The reaction can be accomplished by allowing both stages to proceed consecutively at suitable temperature and pressure, or alternatively the reaction can be stopped at the end of the first phase where the product is glycol aldehyde and the second phase can be carried out under any applicable reduction process which will result in conversion of the aldehyde group of glycol aldehyde to a primary alcohol group resulting in ethylene glycol.

A wide variety of reduction processes can be employed for the second phase reaction including the well-known chemical reducing agents employed in reducing aldehydes to primary alcohols. For commercial processes, however, where possible, catalytic reductions employing hydrogen are usually preferred since they are more practical and efficient especially with catalysts which can be regenerated and thus are re-usable. In the present process, catalytic hydrogenation is preferred for these same reasons, especially with catalysts which can be regenerated. Any hydrogenation catalyst can be employed.

Thus, typical hydrogenation catalysts include, for example, Raney Nickel, cobalt, copper chromite, rhodium, palladium, platinum, and similar such metal catalysts, which can be used conveniently on supports such as charcoal silica, alumina, kieselguhr and the like. The conditions of catalytic hydrogenation are well-known and, in general, the reaction can be conducted at temperatures ranging from about 30° to about 150° C., usually at pressures of from about 100 to about 5000 psig. The use of higher temperatures and pressures, though operable, provides no special advantage and usually requires special equipment which economically is disadvantageous and therefore not preferred.

Particularly preferred catalysts are those which characteristically require short reaction times, e.g. palladium and nickel, which is most desirable for commercial processes for economic reasons.

As mentioned hereinbefore, the main product of the first stage reaction is glycol aldehyde, along with methanol. Glycol aldehyde tends to form acetals, a reaction typical of aldehydes, and in view of the primary alcohol group present in the molecule, this compound forms hemi-acetals and acetals with itself in the form of, for example, linear and cyclic acetals, represented by the formulas:

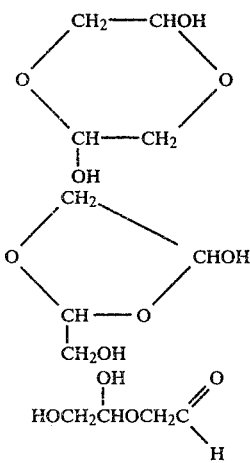

In addition, glycol aldehyde forms acetals and hemi-acetals with methanol, and, if present, ethylene glycol. Acetals in particular are resistant to hydrogenation and should preferably be hydrolyzed to the free aldehyde so that efficient reduction to ethylene glycol can be effected.

The hydrolysis reaction can be accomplished merely by assuring the presence of water in the reaction mixture, preferably in at least equivalent molar quantities. Thus, equimolar amounts of water are required to assure complete hydrolysis, with less than equimolar resulting in less than complete hydrolysis of the acetal present in the mixture which, in turn, results in lower yield of ethylene glycol. It is convenient to hydrolyze the acetal immediately prior to and/or concurrent with the reduction stage.

Oftentimes, the amount of water required for substantial hydrolysis of the aforementioned acetals may already be present in the first stage reaction which ideally contains small amounts of water for best results, e.g. from about 0.5 to about 10% by volume. Alternatively, where insufficient water is present, the necessary water level can be achieved by mere addition of water to the second stage reaction, either batchwise or by metering over the course of the reaction. In experience to the present time, optimum final levels of water are in the range of from about 10–30% by volume based on the hydrogenation mixture.

To facilitate hydrolysis, the presence of an acid is particularly desirable. Thus, strong mineral acids, such as hydrohalic acids, sulfuric, and phosphoric acids or, preferably, weak organic acids, especially lower alkanoic acids such as acetic and propionic acids, can be employed for this purpose. Strong mineral acids should be avoided where the reaction solvent is reactive therewith, e.g. amide solvents which hydrolyze. As will be apparent from the following disclosure, amide solvents are usually preferred, particularly in the first stage reaction and with these solvents, it is preferred to employ weak acids to catalyze the acetal hydrolysis. The amount of acid employed does not appear to be critical and even trace amounts are effective, as should be obvious to those skilled in this art.

Thus, it is apparent that a separate hydrolysis step is not always necessary since the normal water content of the first stage reaction will hydrolyze at least part of the acetals produced and the hydrolyzed part will reduce to ethylene glycol. However, maximizing yield of ethylene glycol dictates the inclusion of a hydrolysis step to assure maximum hydrolysis and thus the highest realizable yield of ethylene glycol. Accordingly, the inclusion of the hydrolysis step, though not always essential, amounts to good technique, which, in view of the simplicity of adding water, with or without acid present, is readily practicable.

The combined hydrolysis-hydrogenation step can be carried out by art-recognized techniques as described, for example, in U.S. Pat. Nos. 4,024,197; 2,721,223; 2,888,492 and 2,729,650 incorporated herein by reference for the disclosed combined reactions.

The catalyst for the first stage reaction may be elemental rhodium, or a rhodium compound, complex or salt, or mixtures thereof, employed as such or deposited or affixed to a solid support such as molecular sieve zeolites, alumina, silica, anion exchange resin or a polymeric ligand. In the active form, the catalyst comprises rhodium in complex combination with carbon monoxide, i.e., rhodium carbonyl, which may contain additional ligands as described, for example, in U.S. Pat. No. 3,527,809 and the aforementioned U.S. Pat. No. 3,833,634, each of which is incorporated herein by reference for the disclosure of rhodium complexes containing carbon monoxide and organic ligands as well as hydrogen as a ligand. As described in U.S. Pat. No. 3,833,634, suitable organic ligands are compounds which contain at least one nitrogen and/or at least one oxygen atom, said atoms having a pair of electrons available for formation of coordinate bonds with rhodium. Illustrative organic ligands include various piperazines, dipyridyls, N-substituted diamines, aminopyridines, glycolic acid, alkoxy-substituted acetic acids; tetrahydrofuran, dioxane, 1,2-dimethoxybenzene, alkyl ethers of alkylene glycols, alkanolamines, iminodiacetic acid, nitrilotriacetic acid, ethylenediaminetetraacetic acid, and the like. In U.S. Pat. No. 3,527,809 are described phosphorus-containing ligands such as trialkyl, triaryl and tricycloalkyl phosphites and triarylphosphines, as well as the analogous antimony and arsenic compounds.

Especially preferred catalysts are those including phosphines as ligand, particularly triaryl phosphines, such as triphenyl phosphine. Illustrative catalysts are well-known and described in the scientific literature. Most preferred of such catalysts are those which include halide, preferably chloride, which result in higher yield of glycol aldehyde in shorter reaction times than corresponding nonchloride-containing catalysts.

The phosphine-containing catalysts can be prepared by the methods described in the aforesaid U.S. Pat. No. 3,527,809 employing suitable ligands exemplified as follows:

| | |
|---|---|
| Trimethylphosphine | Ethyl-bis(beta-phenylethyl) phosphine |
| Triethylphosphine | Tricyclopentylphosphine |
| Tri-n-butylphosphine | Tricyclohexylphosphine |
| Triamylphosphines | Dimethyl-cyclopentylphosphine |
| Trihexylphosphines | Tri-octylphosphine |
| Tripropylphosphine | Dicyclohexylmethylphosphine |
| Trinonylphosphines | Phenyldiethylphosphine |
| Tridecylphosphines | Dicyclohexylphenylphosphine |
| Triethylhexylphosphine | Diphenyl-methylphosphine |
| Di-n-butyl octadecylphosphine | Diphenyl-butylphosphine |
| Dimethyl-ethylphosphine | Diphenyl-benzylphosphine |
| Diamylethylphosphine | Trilaurylphosphine |
| Tris(dimethylphenyl)phosphine | Triphenylphosphine |

Using this procedure, preferred catalysts can be prepared by selection of suitable ligands and rhodium compounds, including the following:
RhCl(CO)(PPh$_3$)$_2$
RhCl(PPh$_3$)$_3$
RhBr(CO)(PPh$_3$)$_2$
RhI(CO)(PPh$_3$)$_2$
RhCl(CO)(PEt$_3$)$_2$
RhCl(CO)[P(p-MeC$_6$H$_4$)$_3$]$_2$
RhCl(CO)[P(p-MeOC$_6$H$_4$)$_3$]$_2$
RhCl(CO)[P(p-FC$_6$H$_4$)$_3$]$_2$
RhCl$_3$(CO)(PPh$_3$)$_2$
RhCl$_3$(PEt$_2$Ph)$_3$
Rh(CO)H(PPh$_3$)$_3$
RhCl(CO)(PEt$_2$Ph)$_2$ The catalyst can be employed in soluble form or in suspension in the reaction medium, or alternatively deposited on porous supports. The catalyst can be prepared by various techniques. For example, the complex with carbon monoxide can be preformed and then introduced into the reaction medium, or, alternatively, the catalyst can be formed in situ by reaction of rhodium, or rhodium compound, directly with carbon monoxide which may be effected in the presence of a selected organic ligand to form the organic ligand-carbon monoxide-rhodium complexes in the reaction medium.

When glycol aldehyde is the desired product, of course, only the first stage reaction need be carried out. The product obtained is usually in the form of the aforementioned acetals and can be separated from the co-produced methanol and reaction solvent, if necessary, by fractional distillation. Gas chromatography and mass spectrophotometric analysis are used to identify the product as glycol aldehyde. In addition, the dimedone (5,5-dimethylcyclohexand-1,3-dione) derivative of pure glycol aldehyde was prepared and compared with the dimedone derivative of the product obtained from the typical reaction according to the present process to show them to be identical. NMR analysis of the derivative confirmed glycol aldehyde as the product. No glyoxal was detected by any of the aforementioned analytical techniques.

The first stage reaction which results in glycol aldehyde, and methanol, production is usually substantially complete in relatively short reaction times, usually less than about one hour, with substantial yield of product realized in as little as 30 minutes, and even less time. Usually, only small amounts of ethylene glycol, if any, can be detected.

As should be apparent, the rhodium catalyst employed in the first stage reaction can also serve as the hydrogenation catalyst for the second stage reaction to produce ethylene glycol. Thus, if the first phase reaction is allowed to continue, eventually the hydrogenation reaction will yield ethylene glycol. Particularly excellent yields are obtained by adding water, where necessary, to hydrolyze the glycol aldehyde acetals present from the first stage reaction thus realizing maximum yields of ethylene glycol. In general, the rhodium catalyst of the first stage reaction is an effective catalyst for the second stage hydrogenation, but does not provide as short reaction times as can be realized with other hydrogenation catalysts, under the usual reaction conditions.

To shorten the second stage reaction time, it is possible to effect the reduction step over metal catalysts such as palladium and nickel, and it is usually preferred to effect the second stage reaction in a separate reactor. Thus, the first stage reaction can be conducted in a first reactor under selected conditions of temperature and pressure, and after completion the first stage product, with or without isolation from the reaction mixture, can then be transferred to a second reactor under selected conditions of temperature and pressure to effect the hydrogenation reaction under hydrolysis conditions, i.e., in the presence of at least the stoichiometric amount of water to hydrolyze the glycol aldehyde acetals present.

Alternatively, the two stage reaction can be conducted in one reactor with provision for controlling the reaction parameters. At the time of the hydrogenation stage, the selected hydrogenation catalyst can be added, conveniently with the water required for hydrolysis, if any is needed, and the hydrogenation reaction can then proceed. In this latter modification, the hydrogenation catalyst can be added to the first phase reaction mixture with or without the first phase rhodium catalyst being present. Generally, it is preferred to remove the rhodium catalyst, particularly if this can be done conveniently so that competitive catalysis will not impede the hydrogenation reaction, and, more importantly, to permit more accurate control over the reaction.

The present invention, therefore, provides a simplified process for selective production of glycol aldehyde as the sole detectable aldehyde product. In addition, this invention affords a simplified process for obtaining ethylene glycol by either allowing the initial process for glycol aldehyde to continue so that hydrogenation under hydrolytic conditions yields ethylene glycol or, alternatively, the glycol aldehyde product of the first stage reaction is reduced under hydrolytic conditions employing art-recognized reduction processes to ethylene glycol. In the latter process, the glycol aldehyde product of the first stage reaction can be used in the form of the reaction mixture, or the product can be isolated, as by fractionation, and used in purified form.

The amount of catalyst employed in the first stage reaction does not seem to be critical and can vary considerably. At least a catalytically effective amount of catalyst should be used, of course. In general, an amount of catalyst which is effective to provide a reasonable reaction rate is sufficient. As little as 0.001 gram atoms of rhodium per liter of reaction medium can suffice while amounts in excess of 0.1 gram atoms do not appear to materially affect the rate of reaction. For most purposes, the effective preferred amount of catalyst is in the range of from about 0.002 to about 0.025 gram atoms per liter.

The reaction conditions are not overly critical in that wide ranges of elevated temperature and superatmospheric pressures are operable. The practical limitations of production equipment will dictate to a great extent the selection of temperatures and pressure at which the reaction is to be effected. Thus, using available production systems, the selected elevated temperature should be at least about 75° C. and can range up to about 250° C. and even higher. For most purposes, the preferred operating temperature ranges from about 100° to about 175° C. The superatmospheric pressure should be at least about 10 atmospheres and can range up to almost any pressure attainable with production apparatus. Since extremely high pressure apparatus is quite expensive, pressures to about 700 atmospheres are suggested. Most desirably, the pressure should be in the range of from about 150 to about 400 atmospheres, particularly when employing the aforesaid preferred temperature range.

The reaction is preferably carried out in a solvent which will dissolve polar materials and which preferably is aprotic in order to maximize selectivity to ethylene glycol. Suitable solvents include a wide variety and are exemplified by N-substituted amides in which each hydrogen of the amido nitrogen is substituted by a hydrocarbon group, e.g., 1-methylpyrrolidin-2-one, N,N-dimethylacetamide, N,N-diethylacetamide, N-methylpiperidone, 1,5-dimethylpyrrolidin-2-one, 1-benzylpyrrolidin-2-one, N,N-dimethylpropionamide, hexamethylphosphoric triamide and similar such liquid amides; nitriles, such as acetonitrile, benzonitrile, propionitrile and the like; cyclic ethers such as tetrahydrofuran, dioxane and tetrahydropyran; ethers such as diethyl ether, 1,2-dimethoxybenzene, alkyl ethers of alkylene glycols and polyalkylene glycols, e.g., methyl ethers of ethylene glycol, propylene glycol and di-, tri- and tetraethylene glycols; ketones such as acetone, methyl isobutyl ketone, and cyclohexanone; esters, such as ethyl acetate, ethyl propionate and methyl laurate; lactones of organic carboxylic acids such as butyrolactone and valerolactone organic acids such as acetic acid, propionic acid and caproic acid; and alkanols, such as methanol, ethanol, propanol, 2-ethylhexanol and the like; and mixtures thereof. Many of the solvents are non-reactive in the medium whereas others are capable of functioning as ligands. The selected solvent should preferably be liquid under the reaction conditions.

When employed, solvents appear to exert varying influences on the yield of product formed and the selectivity to ethylene glycol, depending on the nature of the solvent. For example, when lower alkanoic acids, e.g., acetic acid, are present for example as a co-solvent in the first stage reaction the reaction appears to proceed more rapidly but the yield of glycol decreases somewhat while that of methanol increases. When acetic acid was employed at a level of from about 10 to about 20 volume percent of the reaction mixture, the reaction proceeded in about one-half the time required for the same solvent containing no acetic acid but with increased methanol production (55% vs. 40%) and decreased glycol production (30% vs. 48%). Further, basic amines such as pyridine, triethylamine and amines of comparable basicity appear to exert a negative influence on the yield of glycol aldehyde obtained and this influence becomes more pronounced as the molar ratio of amine to rhodium increases. Thus, even when the amine is present as a co-solvent, the tendency is towards reduced yield of glycol aldehyde when compared to solvent systems from which amines are excluded. Protic solvents such as water, phenols and carboxylic acids, e.g., acetic acid, in large quantities, e.g. greater than about 30–40% by volume, exert a similar negative influence on the yield of glycol aldehyde. In most cases, the decrease in yield of glycol aldehyde is accompanied by an increase in methanol yield, while in some cases the conversion of formaldehyde is reduced so that the yield of both products is reduced. Thus, where optimum yields of glycol aldehyde and ethylene glycol and minimum yields of methanol are desired, basic amines or protic solvents in significant amounts are usually avoided, particularly in the first stage reaction.

On the other hand, certain solvent systems favor high selectivity for glycol aldehyde and ethylene glycol production, and in many cases substantially lower yields of methanol are obtained. Solvents such as organic amides, in particular, favor high selectivity for glycol aldehyde and ethylene glycol production, and in many cases substantially lower yields of methanol are obtained, for which reason these solvents are preferred. Hydrocarbon solvents can be employed but apparently result in lower yields of glycol aldehyde and glycol than obtained with the preferred solvents.

The preferred solvents are aprotic organic amides. The contemplated amides include cyclic amides, i.e. in which the amido group is part of a ring structure such as in pyrrolidinones and piperidones; acylated cyclic amines, such as N-acyl piperidines, pyrroles, pyrrolidines, piperazines, morpholines, and the like, preferably in which the acyl group is derived from a lower alkanoic acid, e.g. acetic acid; as well as acyclic amides, i.e., wherein the amido group is not part of a ring structure as in acetamides, formamides, propionamides, caproamides and the like. The most preferred of the amides are those in which the amido hydrogen atoms are fully replaced by hydrocarbon groups preferably containing not more than 8 carbon atoms. Exemplary hydrocarbon groups are alkyl, preferably lower alkyl such as methyl, ethyl and butyl; aralkyl, such as benzyl and phenethyl; cycloalkyl, such as cyclopentyl and cyclohexyl; and alkenyl, such as allyl and pentenyl. The preferred amido nitrogen substituents are lower alkyl, especially methyl, ethyl and propyl groups and aralkyl groups, especially benzyl. The most preferred amide solvents include 1- methylpyrrolidin-2-one, 1-ethylpyrrolidin-2-one, 1-benzylpyrrolidin-2-one, N,N-diethylacetamide, and N,N-diethylpropionamide.

The nitrile solvents include any organic nitrile solvent preferably containing up to about 8 carbon atoms, such as acetonitrile, benzonitrile, phenylacetonitrile, capronitrile and the like. Mixtures of solvents can be employed.

The reaction pressures represent the total pressure of the gases contained in the reactor, i.e., carbon monoxide and $H_2$, and, if present, any inert diluent gas such as nitrogen. As in any gaseous system, the total pressure is the sum of partial pressures of component gases. In the present reaction, the molar ratio of hydrogen to carbon monoxide can range from about 1/10 to about 10/1, with the preferred ratio, from about 1/5 to about 5/1, and the reaction pressure can be achieved by adjusting the pressure of these gases in the reactor.

For best results, the molar ratio of carbon monoxide to hydrogen is maintained at high values in the first stage reaction where high partial pressures of carbon monoxide favor production of glycol aldehyde. In the second stage reaction, high partial pressure of hydrogen is desirable for reduction reaction. Thus, in the first stage reaction to produce glycol aldehyde, the partial pressure of carbon monoxide is usually adjusted to be about 3 to about 10 times that of hydrogen. In the second stage reaction, i.e. the hydrogenation, the partial pressure of hydrogen is adjusted to a high value to facilitate the reaction. Such adjustments of the gas feed can be readily accomplished. For example, after the first phase reaction is substantially complete, the reactor need only be bled to lower the pressure and then pressurized with hydrogen gas to achieve the desired high partial pressure of hydrogen. Carbon monoxide present in the gaseous system of the first phase reaction need not be completely purged from the reactor prior to repressurizing with hydrogen gas. Of course, carbon monoxide can reduce the efficiency of certain catalyst systems, possibly through poisoning as is known, and preferably is excluded when such systems are employed.

Where the second phase reaction is carried out in a separate reactor whether over the originally present rhodium catalyst or a different metal hydrogenation catalyst, the reaction is normally conducted under hydrogen gas without diluent gas, as is usual in catalyzed hydrogenation reactions.

The source of formaldehyde for the present process can be any of those commonly used in this technology including paraformaldehyde, methylal, formalin solutions, and polyoxymethylenes. Of these, paraformaldehyde is preferred since best yields are attained therewith. Solutions of formaldehyde in solvents, advantageously the reaction solvent, can be used, e.g. solutions of formaldehyde in aqueous reaction solvent, such as N-methyl pyrrolidin-2-one. The use of methylal may be attended by a reduction in yield of ethylene glycol. If trioxane is employed, because of its stability, a hydrolyzing agent should be employed to release formaldehyde.

As with any process of this kind, the present process can be conducted in batch, semi-continuous, and continuous operation. The reactor should be constructed of materials which will withstand the temperatures and pressures required, and the internal surfaces of the reactor are substantially inert. The usual controls can be provided to permit control of the reaction such as heat exchangers and the like. The reactor should be provided with adequate means for agitating the reaction mixture; mixing can be induced by vibration, shaking, stirring, oscillation and like methods. Catalyst as well as reactants may be introduced into the first stage or the second stage reactor at any time during the process for replenishment. Recovered catalyst, solvent and unreacted starting materials may be recycled.

The relative yields of ethylene glycol and methanol are not overly critical since the product mixture can be readily separated into the components by known techniques, especially by fractional distillation, regardless of the proportions contained in the mixture. Therefore, even where ethylene glycol is 10–20% of the reaction mixture, it can be readily separated from the mixture, especially in continuous process production of ethylene glycol, with the methanol recycled as formaldehyde. Of course, the preferred processes yield mixtures in which ethylene glycol predominates as the reaction product.

In addition to the aforementioned solvent effects, other factors also affect the yields of ethylene glycol and methanol and the conversion of formaldehyde in the process. For example, in the combined two-stage reaction, the use of low partial pressures of carbon monoxide appears to favor greater methanol production, whereas the use of high partial pressure of CO, particularly during the first stage, results in lower methanol yields without significant change in glycol yield. Thus, at a partial pressure of carbon monoxide at 1900 psig., the conversion of formaldehyde amounted to 57% with a 76% molar selectivity for ethylene glycol whereas at 1055 psig., the conversion was 72% and molar selectivity was 56% under otherwise identical conditions. Increased partial pressure of hydrogen particularly in the combined reaction resulted in increased glycol selectivity and increased conversion of formaldehyde with little, if any, change in methanol yield.

The effect of temperature variation in the preferred temperature range is not as pronounced, with higher formaldehyde conversion and ethylene glycol selectively being obtained in the 100°–175° C. range, particularly during the first stage reaction.

The process conditions for the separate first stage reaction are essentially the same as employed in the first stage of the combined two-stage reaction. Thus, the reaction is carried out at a temperature of at least about 100° C. to obtain a reasonable reaction rate although somewhat lower temperatures can be employed with slower reaction rates being realized. For reaction times of about one hour, and even less, the temperature should be in the range of from about 100° C. to about 175° C., preferably from about 120° to about 160° C. As in the combined two stage reaction, the partial pressure of carbon monoxide is preferably high, in comparison to that of hydrogen, with the preferred ratios being from about 2:1 to about 10:1, the more preferred being from about 3:1 to about 8:1. The total pressure of gas used is generally maintained at from about 1000 psi up to about 9000 psi, with from about 3000 to about 7000 psi being preferred. Of course, higher pressures and higher temperatures can be used but with no appreciable advantage and, since they require the use of special high pressure equipment, they are usually avoided.

The reaction conditions employed in the second stage reaction, i.e., the hydrogenation, can be any of the standard reaction temperatures and pressures employed for such reactions since neither temperature nor pressure are critical for this reaction. Preferably, the hydrogenation is conducted at a temperature of at least about 100° C. in order to effect a reasonable reaction rate. Of course, lower temperatures can be used if longer reaction times can be tolerated. The pressure of hydrogen gas is not excessively critical as long as sufficient gas is available for the hydrogenation. For convenience, the pressure will range from about 500 psi to as much as 5000 psi, although even higher pressures can be employed.

When the catalyst selected for the hydrogenation step is other than rhodium, it is preferred to remove the rhodium catalyst from the first stage reaction mixture. This preference is primarily predicated on the desirability of avoiding concomitant catalytic effects which may tend to reduce the yield of ethylene glycol, the desired product. It has been determined, for example, that the yield of ethylene glycol was considerably lessened when the hydrogenation was effected over supported nickel or palladium catalyst using the first stage reaction mixture without removing the rhodium catalyst present therein. When these hydrogenations were repeated with the addition of water to the reaction mixture, the water preferably containing at least catalytic amounts of acid, usually acetic acid, almost quantitive conversion to ethylene glycol occurred, particularly when Palladium catalyst, e.g. Pd/C, is used. However, after the glycol aldehyde is separated from rhodium catalyst, e.g. by distillation, the glycol aldehyde is reduced almost quantitatively with catalysts such as palladium on carbon in the absence or presence of rhodium. The aforesaid reduced yields of ethylene glycol are explainable by the production of unidentified high boiling liquid product which remains after distillation of ethylene glycol from the reaction mixture. Apparently, secondary competitive reactions proceed where both the rhodium catalyst and the hydrogenation metal catalyst are simultaneously present in the hydrogenation reaction mixture, the nature of which reactions is not understood up to the present. Surprisingly, no significant amounts of the high boiling residue was discovered in the reactions mixtures obtained with either rhodium or other metal as the sole hydrogenation catalyst. With Pd/C, glycol aldehyde is almost quantitatively reduced to ethylene glycol.

The results obtained with the present new process are surprising and totally unexpected. As hereinbefore described, the prior art processes of reacting formaldehyde, carbon monoxide and hydrogen have led to mixtures of polyol products principally ethylene glycol, glycerol and higher diols from which it is extremely difficult to separate the individual components. The present process on the other hand, selectively yields ethylene glycol as the polyol product. Analysis of the product produced by means of gas-liquid chromatography has failed to reveal any polyol other than ethylene glycol, which is readily separated from methanol, the monohydric alcohol product, as hereinbefore mentioned.

The following examples further illustrate the invention.

EXAMPLE 1

A 71 ml. stainless steel reactor fitted with a glass liner is charged with 0.5 g of commercial paraformaldehyde 0.019 g $Rh(CO)_2(C_5H_7O_2)$ and 5 ml. N-methylpyrrolidinone. The reactor is pressured to 4350 psig with $H_2$ and CO at a ratio of 2.2/1 and then shaken by a wrist action shaker in a hot air oven at 150° C. for five hours. After cooling and venting the gases, the reaction mixture is analyzed via gas-liquid chromatography and is found to contain 0.07 g. of methanol and 0.43 g. of ethylene glycol. No higher polyols are observed.

EXAMPLE 2

The reaction is carried out as in Example 1 except the reactor is pressured to 3350 psig with $H_2$ and CO at a ratio of 1.5/1. The reaction solution is analyzed and found to contain 0.08 g. of methanol and 0.34 g. of ethylene glycol. Identification of ethylene glycol is confirmed by mass spectrometry.

EXAMPLE 3

The reaction is carried out as in Example 1 except the reactor is pressured to 2350 psig with $H_2$ and CO at a ratio of 1.7/1. Analysis after the reaction shows the presence of 0.07 g. of methanol and 0.25 g. of ethylene glycol.

EXAMPLE 4

The reaction is carried out as in Example 1 except that 2.5 g. of methylal is charged in place of paraformaldehyde and the reactor is pressured to 3330 psig. with $H_2$ and CO at a ratio of 1.5/1. Analysis of the solution after reaction shows the presence of 0.26 g. of methanol and 0.06 g. of ethylene glycol.

EXAMPLE 5

The reaction is carried out as in Example 1 except the reactor is pressured to 3750 psig. with $H_2$ and CO at a ratio of 4/1. Analysis of the reaction mixture shows the presence of 0.16 g. of methanol and 0.40 g. of ethylene glycol.

EXAMPLE 6

The reaction is carried out as in Example 2 except the formaldehyde is charged as 1.28 g. of 37% aqueous solution stabilized with methanol. Analysis of the reaction solution shows the presence of 0.29 g. of methanol (after correcting for the initial methanol) and 0.25 g. of ethylene glycol.

EXAMPLE 7

The reaction is carried out as in Example 1 except the formaldehyde is charged as 0.5 g. of alkali precipitated α-polyoxymethylene and the reactor is pressured to 3500 psig. with $H_2$ and CO at a ratio of 2.3/1. Analysis of the reaction solution shows the presence of 0.17 g. of methanol and 0.30 g. of ethylene glycol.

EXAMPLE 8

The reaction is carried out as in Example 2 except the reaction temperature is 175° C. Analysis of the reaction solution shows the presence of 0.06 g. of methanol and 0.25 g. of ethylene glycol.

EXAMPLE 9

The reaction is carried out as in Example 2 except the reaction temperature is 125° C. Analysis of the reaction solution shows the presence of 0.08 g. of methanol and 0.33 g. of ethylene glycol.

EXAMPLE 10

A 71 ml. stainless steel reactor equipped with a glass liner is charged with 0.037 g $Rh(CO)_2(C_5H_7O_2)$, 1.0 g. paraformaldehyde and 5 ml. N-methylpyrrolidinone, pressured to 3000 psig. with $H_2$ and CO in a ratio of 1.5/1, and shaken ten hours at 200° C. After cooling and venting the gases analysis of the reaction solution shows the presence of 0.51 g. of methanol and 0.16 g. of ethylene glycol.

EXAMPLE 11

The reaction is carried out as in Example 10 except the charge is 0.037 g. $Rh(CO)_2(C_5H_7O_2)$, 1.0 g. paraformaldehyde and 5 ml. of hexamethylphosphoric triamide, and the pressure is 3330 psig with $H_2$ and CO in a ratio of 1.5/1. The reaction is carried out for five hours at 150° C. Analysis of the reaction solution shows the presence of 0.58 g. of methanol and 0.20 g. of ethylene glycol.

EXAMPLE 12

The reaction is carried out as in Example 11 except the solvent is N,N-dimethylacetamide. Analysis of the reaction product shows the presence of 0.64 g. of methanol and 0.32 g. of ethylene glycol.

EXAMPLE 13

The reaction is carried out as in Example 2 except the solvent is acetonitrile. Analysis of the reaction product shows the presence of 0.10 g. of methanol and 0.14 g. of ethylene glycol.

EXAMPLE 14

The reaction is carried out as in Example 2 except the solvent is N-methylpiperidone. Analysis of the reaction product shows the presence of 0.32 g. of methanol and 0.16 g. of ethylene glycol.

EXAMPLE 15

The reaction is carried out as in Example 2 except the solvent is N-benzylpyrrolidinone. Analysis of the reaction product shows the presence of 0.28 g. of methanol and 0.09 g. of ethylene glycol.

EXAMPLE 16

The reaction is carried out as in Example 7 except the solvent is N,N-diethylacetamide and the formaldehyde is charged as 0.5 g. of paraformaldehyde. Analysis of the reaction product shows the presence of 0.05 g. of methanol and 0.29 g. of ethylene glycol.

EXAMPLE 17

The reaction is carried out as in Example 16 except the solvent is 1,5-dimethyl-2-pyrrolidinone. Analysis of the reaction product shows the presence of 0.35 g. of methanol and 0.17 g. of ethylene glycol.

EXAMPLE 18

The reaction is carried out as in Example 7 except that the formaldehyde is charged as paraformaldehyde, the solvent is 1,4-dioxane and the $H_2$/CO ratio is 2.0/1. Analysis of the reaction product shows the presence of 0.07 g. of methanol and 0.16 g. of ethylene glycol.

EXAMPLE 19

The reaction is carried out as in Example 18 except the solvent is benzonitrile. Analysis of the reaction product shows the presence of 0.13 g. of methanol and 0.1 g. of ethylene glycol.

EXAMPLE 20

A 300 ml. Magne-Stir autoclave equipped with a Disperso-Max stirrer which was operated at 1500 rpm was charged with 0.285 g. of $Rh(CO)_2(C_5H_7O_2)$, 7.5 g. of 95% paraformaldehyde and 75 ml of N-methylpyrrolidinone. The reactor is closed and, while the solution is stirred, pressured to 3500 psig with $H_2$ and CO at a 3/1 ratio. The reactor is heated to 150° C. Maximum pressure of 4650 psig is reached at 138° C. When the pressure drops to 4100 psig, the reactor is repressured to 5000 psig with $H_2$ and CO at a 2/1 ratio. Total reaction time at 150° C. is 3 hours. After cooling and venting the reactor is opened and the product solution recovered. Analysis of the product shows the presence of 3.0 g. of methanol and 6.0 g. of ethylene glycol.

EXAMPLE 21

The procedure of Example 20 is repeated except that the autoclave is pressured to give 5000 psig at 125° C. with $H_2$ and CO at a ratio of 1.86/1. The reactor is heated, with stirring at 1500 rpm, to 125° C. When the pressure drops to 4200 psig, the autoclave is repressured to 5000 psig with the same gas mixture. The total time at 125° C. is five hours. Analysis of the product solution shows the presence of 1.3 g. of methanol and 6.6 g. of ethylene glycol.

EXAMPLE 22

The reaction is carried out as in Example 21 except the $H_2$ and CO were at a ratio of 1/1 and at an initial pressure of 5200 psig at 125° C. Analysis of the product solution shows the presence of 4.2 g of methanol and 2.8 g. of ethylene glycol.

EXAMPLE 23

The reaction is carried out as in Example 21 except that 0.143 g. of $Rh(CO)_2(C_5H_7O_2)$ is charged. Analysis of the product solution shows the presence of 1.3 g. of methanol and 1.8 g. of ethylene glycol.

EXAMPLE 24

The reaction is carried out as in Example 21 except that 0.428 g. of $Rh(CO)_2(C_5H_7O_2)$ is charged and the reaction time is three hours. Analysis of the product solution shows the presence of 1.0 g. of methanol and 6.3 g. of ethylene glycol.

EXAMPLE 25

The reaction is carried out as in Example 1 except the catalyst is charged as 0.008 g. powdered elemental rhodium and the temperature is 250° C. Analysis of the product solution shows the presence of 0.32 g. of methanol and 0.17 g. of ethylene glycol.

EXAMPLE 26

The reaction is carried out as in Example 2 except the catalyst is charged as 0.067 g. $RhH(CO)[P(C_6H_5)_3]_3$. Analysis of the product solution shows the presence of 0.16 g. of methanol and 0.11 g. of ethylene glycol.

EXAMPLE 27

The procedure of Example 25 is repeated using rhodium oxide and rhodium chloride, respectively, in lieu of elemental rhodium with comparable results.

EXAMPLE 28

The procedure of Example I is repeated except the solvent is N,N-diethylpropionamide. Analysis of the product shows 0.02 g. methanol and 0.18 g. ethylene glycol.

EXAMPLE 29

The procedure of Example I is repeated except the solvent is N-ethylpyrrolidin-2-one. Analysis of the product shows 0.17 g. methanol and 0.38 g. ethylene glycol.

EXAMPLE 30

The procedure of Example I is repeated except the solvent is N,N-diethyl-m-toluamide. Analysis of the product shows 0.07 g. methanol and 0.17 g. ethylene glycol.

In each of the foregoing examples, the analyses were carried out using gas-liquid chromatography and in no instance was there any polyol, excepting ethylene glycol, detected.

The amide solvents used in the foregoing examples were freed of amine contaminants by distillation.

As mentioned hereinbefore, amines appear to show a negative influence on the yield of glycol and thus are preferably avoided. Accordingly, amine solvents and amine ligands for the rhodium carbonyl complex are not employed because of the said negative influence which can result in little, if any, yield of the desired ethylene glycol depending on the amount of amine present. Thus, when pyridine is present in the reaction mixture, the yield of ethylene glycol is appreciably diminished, the extent of diminution of yield being proportional to the molar ratio of pyridine to rhodium; when hydroxypyridine is used as ligand for the rhodium carbonyl complex a similar diminution of yield of ethylene glycol is observed. The following examples illustrates the negative influence of amines on the present process.

EXAMPLE 31

The procedure of Example I is repeated using 0.073 millimole $Rh(CO)_2(C_5H_7O_2)$ and 15.8 millimoles paraformaldehyde in 5 ml. N-methylpyrrolidin-2-one which is stirred for 5 hours at 150° C. The initial pressure is 5000 psig ($H_2/CO=2.2$).

Using this procedure, the effect of addition of various levels of pyridine is determined and the results given in Table I.

TABLE I

| Expt. No. | Pyridine Added moles/mole Rh | % Yield (Glycol and Methanol) | Productivity moles/mole Rh | |
|---|---|---|---|---|
| | | | Glycol | Methanol |
| 1 | 0 | 47 | 70 | 42 |
| 2 | 0.16 | 67 | 45 | 114 |
| 3 | 0.3 | 80 | 26 | 163 |
| 4 | 1.0 | 75 | 11 | 167 |

From these data, it is apparent that pyridine exerts a negative influence on the ethylene glycol yield. Similar results are obtained with other amines such as methylamine, triethylamine and 2-hydroxypyridine.

The effect of hydrogen and carbon monoxide partial pressures, previously discussed herein, is demonstrated by the data of Table II which is determined by repeating the procedure of Example 31 without amine present but varying the gaseous components.

TABLE II

| Expt. No. | Initial Partial Pressures, psi | | % Yield (Glycol + Methanol) | Productivity Moles/mole Rh | |
|---|---|---|---|---|---|
| | $H_2$ | CO | | Glycol | Methanol |
| 1 | 1410 | 1900 | 38 | 51 | 30 |
| 2 | 2850 | 1900 | 45 | 74 | 23 |
| 3 | 4250 | 1900 | 57 | 93 | 30 |
| 4 | 4250 | 1055 | 72 | 89 | 68 |

Variation in reaction temperature provides a somewhat lesser effect, although fairly pronounced, the lower temperatures providing higher yields of ethylene glycol as illustrated in Table III.

TABLE III

| Expt. No. | Temp. °C. | % Yield (Glycol and Methanol) | Productivity (moles/mole Rh) | |
|---|---|---|---|---|
| | | | Glycol | Methanol |
| 1[1] | 175 | 37 | 56 | 25 |
| 2[1] | 150 | 45 | 74 | 23 |
| 3[1] | 125 | 51 | 74 | 36 |
| 4[2] | 175 | 47 | 68 | 34 |
| 5[2] | 150 | 57 | 77 | 46 |
| 6[3] | 125 | 62 | 98 | 37 |

[1] 5 hrs in 71 ml shaken reactor-$Rh(CO)_2(C_5H_7O_2)$, 0.073 millimole; paraformaldehyde, 15.8 millimoles; N-methylpyrrolidinone, 5 ml; $H_2$:CO, 3:2 at 4760 psi (initial).
[2] 3 hrs in 300 ml stirred reactor - $Rh(CO)_2(C_5H_7O_2)$, 1.095 millimole; paraformaldehyde, 237 millimoles, N-methylpyrrolidinone, 75 ml; $H_2$,3250 psi (initial); CO, 1750 psi (initial).
[3] Identical to (2) except 5 hrs.

The following example illustrates the ineffectiveness of rhodium carbonyl catalyst in the reaction of carbon monoxide and hydrogen to produce ethylene glycol and methanol, under the same conditions of temperature and pressure as employed in the preceding examples.

EXAMPLE 32

Using the procedure of the foregoing examples, except that formaldehyde is omitted, a mixture of $Rh(CO)_2(C_5H_7O_2)$ (0.145 millimoles); ligand (when present) (0.57 millimole) and solvent (5 ml.) is heated at an initial pressure of 5000 psig ($H_2/CO=1.5$) and 200° C. with stirring for 10 hours. A series of runs, with and without ligand (2-hydroxypyridine and pyrocatechol) using various solvents including N-methyl pyrrolidin-2-one, tetrahydrofuran, tetraglyme and mixtures thereof with methanol and methyl formate, resulted in no detectable amounts of ethylene glycol and from 0 to 5 millimoles of methanol.

The use of longer or shorter reaction time shows no appreciable change as is also the case when the catalyst is increased to five times the aforestated amount.

The results are summarized in Table IV.

TABLE IV

| | Hydrogenation of CO(1) | | | | |
|---|---|---|---|---|---|
| Expt. No. | Ligand | Solvent | Ethylene Glycol (Millimole) | Methanol (Millimole) | Comments |
| 1 | 2-Hydroxypyridine | THF(2) | 0 | — | (3) |
| 2 | " | TG(4) | 0 | 1.2 | |
| 3 | " | " | 0 | 0.3 | (5) |
| 4 | " | " | 0 | 3.6 | (6) |
| 5 | " | TG + $HCO_2CH_3$ | 0 | 3.2 | |
| 6 | " | TG | 0 | 1.0 | (7) |

TABLE IV-continued

| | | Hydrogenation of CO(1) | | | |
|---|---|---|---|---|---|
| Expt. No. | Ligand | Solvent | Ethylene Glycol (Millimole) | Methanol (Millimole) | Comments |
| 7 | Pyrocatechol | " | 0 | <0.1 | (7) |
| 8 | 2-Hydroxypyridine | TG + CH$_3$OH | 0 | — | |
| 9 | " | TG | 0 | 2.9 | (8) |
| 10 | " | TG + H$_2$C(OCH$_3$)$_2$ | 0 | 5.0 | |
| 11 | " | TG | 0 | 0 | (9) |
| 12 | — | NMP(10) | 0 | 0 | |

(1) 10 hrs at 200° C. in 71 ml reactors; Rh(CO)$_2$(C$_5$H$_7$O$_2$) - 0.145 millimole; ligand - 0.57 millimole; Solvent - 5 ml; 5000 psig initial pressure (H$_2$/CO = 1.5)
(2) THF = tetrahydrofuran
(3) Time = 5 hours
(4) TG = tetraglyme
(5) No glass liner
(6) Five times the usual amount of catalyst and ligand
(7) 225° C.
(8) Time = 64 hours
(9) TG treated with molecular sieves
(10) NMP = N-methylpyrrolidone

EXAMPLE 33

Using the procedure of Example 7 but using paraformaldehyde as formaldehyde source and H$_2$/CO=2.1, a variety of N,N- disubstituted amides are evaluated as solvents with the results summarized in Table V.

TABLE V

| Solvent | Glycol(g) | Methanol(g) |
|---|---|---|
| N,N-dipropylacetamide | 0.11 | 0.01 |
| N,N-dibutylacetamide | 0.09 | 0.03 |
| N-acetyl piperidine | 0.19 | 0.31 |
| N-propyl pyrrolidine-2-one | 0.11 | 0.36 |
| N-butyl pyrrolidin-2-one | 0.03 | 0.32 |
| N-isolpropyl pyrolidin-2-one | 0.17 | 0.31 |
| N-3*butyl pyrolidin-2-one | 0.19 | 0.21 |

The foregoing examples are illustrative of the combined two stage reaction. Example 34 illustrates the production of glycol aldehyde by the first stage reaction.

EXAMPLE 34

The following reaction mixture is charged to a pressure vessel as employed in the preceding examples:
2.5 mmole Rh (CO)$_2$ (C$_7$H$_5$O$_2$)
237 mmole paraformaldehyde (95%)
5 ml. H$_2$O
114 ml. N-methylpyrrolidinone The vessel is pressured to 2500 psi (P$_{co}$=2000 psi and P$_{H2}$=500 psi) and then heated to 130° C. and stirred at 1750 rpm. at a constant pressure.

Samples are removed at 15 minute intervals and analyzed with the following results:

| | YIELDS (mmoles) | | | |
|---|---|---|---|---|
| Reaction Time (min.) | CH$_2$O | Glycol Aldehyde | MeOH | Ethylene Glycol |
| 15 | 163 | 17 | 0 | 0 |
| 30 | 128 | 50 | 19 | 0 |
| 45 | 89 | 81 | 29 | 0 |
| 60 | 63 | 97 | 34 | 0 |
| 75 | 38 | 103 | 45 | 0 |
| 90 | 17 | 113 | 59 | 0 |

The aldehydes present in the final reaction solution are identified as formaldehyde and glycol aldehyde with no other aldehyde or carboxyl compound being detected. Glycol aldehyde can be separated from the reaction mixture, e.g. by distillation, or the reaction mixture can be used in the second stage reaction as in Example 35. When this procedure is repeated at 160° C., the yield of glycol aldehyde decreased substantially after the first 30 minutes. On repeating this procedure at lower total pressure (P$_{co}$=2000 psi and P$_{H2}$=500 psi) slightly lower yield of glycol aldehyde is obtained.

Example 35 illustrates the two stage reaction using the rhodium catalyst as the hydrogenation catalyst.

EXAMPLE 35

The procedure of Example 34 is repeated except that the first stage is terminated at the end of one hour and the vessel depressurized by bleeding and then repressurized with hydrogen to 5000 psi so that the hydrogen is 80 mole % of the total gas. The second stage reaction then proceeds and is sampled at 15 minute intervals for analysis with the following results:

| | | | YIELDS (mmoles) | | |
|---|---|---|---|---|---|
| Experiment | Time | H$_2$CO | Glycol Aldehyde | MeOH | Ethylene Glycol |
| 1 | 30 | 131 | 73 | 19 | 0 |
| | 60 | 64 | 126 | 26 | 0 |
| | 15 | 6 | 93 | 69 | 10 |
| | 30 | <1 | 43 | 78 | 83 |
| | 45 | <1 | 14 | 73 | 112 |
| | 60 | <1 | 6 | 74 | 117 |
| 2 | 30 | 133 | 67 | 19 | 0 |
| | 60 | 55 | 128 | 26 | 0 |
| | 15 | 2 | 78 | 69 | 47 |
| | 30 | <2 | 18 | 73 | 115 |
| | 45 | <2 | 6 | 65 | 117 |
| | 60 | <2 | 6 | 62 | 120 |
| 3 | 30 | 124 | 70 | 0 | 0 |
| | 60 | 34 | 150 | 22 | 0 |
| | 15 | <2 | 14 | 64 | 112 |
| | 30 | <2 | 1 | 78 | 127 |
| | 45 | <2 | 6 | 82 | 127 |
| | 60 | <2 | 6 | 79 | 127 |

In Experiment 2, 10 ml of glacial acetic acid was added to the reaction mixture before the start of the hydrogenation. In Experiment 3, 20 ml. of H$_2$O was added at the beginning of the hydrogenation.

EXAMPLE 36

A pressure vessel is charged with the following:
4 ml. N-methyl pyrrolidinone 7.58 mmole formaldehyde (as paraformaldehyde-95%)
0.7 mmole Rh (CO)$_2$ (C$_7$H$_5$O$_2$)
and the vessel is pressured to 4000 psi with CO (80 mole %) and H$_2$ (20 mole %) and heated at 130° C. for 90 minutes.

The product on analysis showed:
1.2 mmole MeOH
0.5 mmole H$_2$CO
4.7 mmole glycol aldehyde The reaction mixture is then pressurized with hydrogen to 75 mole % H$_2$ and 25 mole % CO and heated at 150° C. for five hours to obtain a product of the following composition:
2.2 mmole MeOH
3.6 mmole ethylene glycol The reduction step is repeated but with 0.5 g. Ni on kieselguhr and 0.5 ml. each of water and acetic acid added to the reaction mixture. The product obtained has the following composition:
1.4 mmole ethylene glycol
1.0 mmole MeOH
and high boiling residue When this procedure is repeated using Pd/C (5%) in lieu of the Nickel catalyst, the product has the following composition:
1.8 mmole ethylene glycol
1.7 mmole MeOH
and high boiling residue When the reduction procedure is repeated but with pure glycol aldehyde using Pd/C with N-methylpyrrolidinone as solvent at hydrogen pressure of 3000 psi for 5 hrs. at 150° C. an almost quantitative yield of ethylene glycol is obtained. Using Nickel on kieselguhr in lieu of Pd/C resulted in lower conversion to ethylene glycol.

The following example shows the results obtained with pure glycol aldehyde in the hydrogenation, as contrasted with Example 36.

EXAMPLE 37

A pressure vessel is charged with the following:
8.3 mmol. glycol aldehyde
4 ml. N-methyl pyrrolidinone
and the selected catalyst system is added. The vessel is then pressurized to 3000 psi H$_2$ and heated at 150° C. for five hours to obtain the hydrogenation product with the following results:

| Run | Catalyst | Additives | Residual aldehyde (mmol.) | Ethylene glycol (mmol.) |
|---|---|---|---|---|
| 1 | Rh(CO)$_2$ (C$_7$H$_5$O$_2$) Pd/C (5%) | — | 0.9 | 2.4 |
| 2 | Rh(CO)$_2$ (C$_7$H$_5$O$_2$) Pd/C (5%) | 50% aq. HOAC | 0.1 | 7.4 |
| 3 | Pd/C (5%) | — | 0 | 9.9 |

The aqueous acetic acid (50%) is present at a level of 20% by volume of the reaction mixture.

The results indicate quantitative conversion to ethylene glycol using Pd/C as the sole hydrogenation catalyst. Further, the results with the combined rhodium and palladium catalysts show that the hydrogenation proceeds substantially better under hydrolytic conditions.

EXAMPLE 38

The following mixture is charged to a pressure vessel as employed in the preceding examples:
0.004 M/l Rh catalyst
1.9 M/l paraformaldehyde (95%)
2.2 M/l H$_2$O
solvent - N-methylpyrrolidinone The vessel is pressured to 5000 psig (4CO:1H$_2$) and heated to 140° C. with stirring at 1750 rpm with periodic sampling to determine reaction extent. Various catalysts are evaluated using this procedure with the following results:

| | Time (min.) | HCHO | HOCH$_2$CHO | MeOH | Ethylene Glycol | % HCHO Accounted |
|---|---|---|---|---|---|---|
| Rh(CO)Cl(Ph$_3$P)$_2$ | 5 | 113 | 76 | 14 | 8 | 89 |
| | 10 | 66 | 120 | 16 | 9 | 89 |
| | 15 | 39 | 140 | 17 | 8 | 86 |
| | 30 | 10 | 160 | 9 | 10 | 80 |
| | 60 | 3 | 151 | 9 | 9 | 73 |
| Rh(CO)H(Ph$_3$P)$_3$ | 5 | 167 | 16 | 11 | 3 | 83 |
| | 10 | 133 | 46 | 19 | 3 | 85 |
| | 15 | 90 | 87 | 18 | 3 | 84 |
| | 30 | 42 | 117 | 34 | 4 | 83 |
| | 60 | 8 | 102 | 32 | 9 | 64 |
| RhCl(Ph$_3$P)$_3$ | 5 | 98 | 86 | 13 | 3 | 84 |
| | 10 | 48 | 142 | 13 | 4 | 87 |
| | 15 | 20 | 168 | 15 | 4 | 87 |
| | 30 | 6 | 175 | 13 | 5 | 84 |
| | 60 | 3 | 170 | 15 | 6 | 82 |
| Rh(CO)$_2$C$_7$H$_5$O$_2$ | 5 | 175 | 0 | 14 | 0 | 77 |
| | 10 | 152 | 15 | 14 | 0 | 76 |
| | 15 | 137 | 30 | 18 | 0 | 78 |
| | 30 | 91 | 53 | 30 | 0 | 82 |
| | 60 | 47 | 103 | 25 | 2 | 75 |

From these data it is apparent that those catalysts with the phosphine ligand present are more efficient than those without such ligand and further that the chloride containing catalysts are most efficient. In particular, the chloride-containing rhodium-phosphines provide fast reaction time best yields (70% and higher) and 80-85% selectivity to ethylene glycol.

By comparison, the process of U.S. Pat. No. 3,920,753 at best yields 50% yield of glycol aldehyde and a selectivity of only about 50%.

From the experimental data, it is apparent that in the present process a high catalyst efficiency is attained as well as a high selectivity to glycol aldehyde in the first stage reaction and to ethylene glycol in the second stage reaction. In general, the optimum average yield of glycol aldehyde based on catalyst employed is about 100 moles/mole of rhodium catalyst. In contrast, in U.S. Pat. No. 3,920,753 the reported experimental results show that an optimum of about 14 moles of glycol aldehyde are produced per mole of cobalt catalyst employed.

In addition, it has been found that the reaction product produced in accordance with the examples of the said U.S. Pat. No. 3,920,753 does not readily catalytically reduce to produce appreciable amount of ethylene glycol unless the cobalt catalyst is separated from the product. Specifically, the reaction product of Example 4 without separating cobalt catalyst was subjected to various hydrogenation conditions and no significant amount of ethylene glycol was obtained. In most cases, no ethylene glycol was detected whereas in a few instances some glycol was produced but not more than 10% yield based on glycol aldehyde contained in the Example 4 reaction product. In all instances, there was noted a reduction in the glycol aldehyde, indicating consumption of the aldehyde apparently forming high-boiling by-products.

Specifically, a comparison of the rhodium-containing reaction product of the present invention with the cobalt-containing reaction product of U.S. Pat. No. 3,920,753 gave the following results:

Hydrogenation conditions: 0.5 g. 5% Pd/C; 30 minutes at 150° C.; 5 ml. $H_2O$ and 5 ml. of reaction product sample.

| | gas (psi) | Methanol | Ethylene Glycol |
|---|---|---|---|
| Rh Catalyst, 4.3 mmole glycol aldehyde | (a) 1000 $H_2$ | 28 | 72 |
| | (b) 1000 $H_2$ 4000 CO | 25 | >100 |
| Co Catalyst 4.9 mmole glycol aldehyde | (a) 1000 $H_2$ | 18 | 0 |
| | (b) 1000 $H_2$ 4000 CO | 6 | 6 |

The resulting products were analyzed for carbonyl, i.e., glycol aldehyde, and the Rh-catalyst containing products showed, respectively, 1% and 0%, whereas the C-catalyst containing products showed 53% and 15%, respectively.

What is claimed is:

1. A process which comprises reacting formaldehyde, carbon monoxide and hydrogen in an aprotic solvent at a temperature of from about 75° C. to about 250° C. and superatmospheric pressure up to about 700 atmospheres to form glycol aldehyde in a first reaction stage and subsequently catalytically reducing the glycol aldehyde to form ethylene glycol in a second reaction stage, wherein a catalytic amount of rhodium in complex combination with carbon monoxide is present at least during said first reaction stage.

2. A process according to claim 1 wherein said rhodium is present during said second reaction stage.

3. A process according to claim 1 wherein a hydrogenation catalyst is present during said second stage reaction.

4. A process according to claim 3 wherein said rhodium is removed from the first reaction stage product prior to said second stage reaction.

5. A process according to claim 3 wherein said hydrogenation catalyst comprises palladium.

6. A process according to claim 1 wherein said first and second stage reactions are conducted at a temperature of from about 100° to about 175° C.

7. A process for producing glycol aldehyde and/or ethyleneblycol which comprises reacting formaldehyde, carbon monoxide and hydrogen in an aprotic solvent at a temperature of from about 75° to about 250° C. and a pressure of from about 10 to about 700 atmospheres in the presence of a catalytic amount of a catalyst comprised of rhodium in complex combination with carbon monoxide and recovering glycol aldehyde and/or ethyleneblycol from said reaction.

8. A process according to claim 7 wherein said catalyst further comprises a tri-organo phosphine ligand.

9. A process according to claim 7 wherein said catalyst further comprises a triaryl phosphine ligand.

10. A process according to claim 7 wherein said temperature is in the range of from about 100° to about 175° C. and said pressure is in the range of from about 150 to about 400 atmospheres.

11. A process according to claim 10 wherein the molar ratio of hydrogen to carbon monoxide is from about 1/10 to about 10/1.

12. A process according to claim 10 wherein the reaction is carried out in the presence of a solvent comprising an aprotic organic amide.

13. A process according to claim 12 wherein the solvent comprises an N-lower alkyl pyrrolidin-2-one.

14. A process according to claim 12 wherein the solvent comprises an N,N-di(lower alkyl)acetamide.

15. A process according to claim 12 wherein the solvent comprises N-methyl pyrrolidin-2-one.

16. A process according to claim 12 wherein the solvent comprises N,N-diethyl acetamide.

17. A process according to claim 12 wherein the solvent comprises N,N-diethyl propionamide.

18. A process of producing ethylene glycol which comprises the steps of:

(A) reacting formaldehyde, carbon monoxide and hydrogen in an aprotic solvent at a temperature of from about 75° to about 250° C. and superatmospheric pressure up to about 700 atmospheres in the presence of a catalytic amount of a catalyst comprised of rhodium in complex combination with carbon monoxide to form glycol aldehyde; and (B) catalytically hydrogenating said glycol aldehyde under hydrolytic conditions to produce ethylene glycol.

19. A process according to claim 18 wherein the solvent comprises an N-lower alkyl pyrrolidin-2-one.

20. A process according to claim 18 wherein the solvent comprises N-methyl pyrrolidin-2-one.

21. A process according to claim 18 wherein the temperature is from about 100° to about 175° C. and the pressure is from about 150 to about 400 atmospheres.

22. A process according to claim 24 wherein the catalyst for said catalytic hydrogenation comprises palladium or rhodium.

23. A process according to claim 24 wherein said hydrogenating is carried out in the presence of aqueous acid.

24. A process according to claim 26 wherein said acid is acetic acid.

* * * * *

UNITED STATES PATENT AND TRADEMARK OFFICE
CERTIFICATE OF CORRECTION

PATENT NO. : 4,200,765
DATED : April 29, 1980
INVENTOR(S) : Richard W. Goetz

It is certified that error appears in the above-identified patent and that said Letters Patent are hereby corrected as shown below:

Claim 22, line 1, "24" should read --18--;

Claim 23, line 1, "24" should read --18--; and,

Claim 24, line 1, "26" should read --23--.

Signed and Sealed this

Second Day of July 1985

[SEAL]

Attest:

DONALD J. QUIGG

Attesting Officer

Acting Commissioner of Patents and Trademarks